United States Patent [19]
Gueirard et al.

[11] Patent Number: 6,030,625
[45] Date of Patent: Feb. 29, 2000

[54] BORDETELLA PERTUSSIS AND BORDETELLA PARAPERTUSSIS STRAINS

[75] Inventors: Pascale Gueirard, Meudon la Foret; Nicole Guiso, Paris, both of France

[73] Assignee: Institut Pasteur, Paris, France

[21] Appl. No.: 09/064,626

[22] Filed: Apr. 23, 1998

Related U.S. Application Data

[63] Continuation of application No. 08/591,799, Jan. 25, 1996, which is a continuation of application No. 08/574,439, Dec. 15, 1995.

[30] Foreign Application Priority Data

Dec. 15, 1994 [FR] France .................................... 9415137

[51] Int. Cl.⁷ .......................... A61K 39/00; A61K 39/02; A61K 39/10; A01N 63/00; C12N 1/00
[52] U.S. Cl. .................................... 424/253.1; 424/184.1; 424/234.1; 424/254.1; 424/93.1; 424/93.4; 424/240.1; 435/243; 435/252.1
[58] Field of Search .............................. 424/184.1, 234.1, 424/253.1, 254.1, 93.1, 93.4, 240.1; 435/243, 252.1

[56] References Cited

U.S. PATENT DOCUMENTS

| | | | |
|---|---|---|---|
| 5,095,094 | 3/1992 | Brezin et al. ............................ | 530/350 |
| 5,595,901 | 1/1997 | Rocancourt et al. ................... | 435/232 |

FOREIGN PATENT DOCUMENTS

| | | |
|---|---|---|
| 0338 170 | 10/1989 | European Pat. Off. . |
| 2 606 789 | 5/1988 | France . |
| WO 90/13312 | 11/1990 | WIPO . |

OTHER PUBLICATIONS

Bartoloni et al., "Engineering Bacterial Toxin for the Development of New Vaccine against Pertussis," *Tokai J. Exp. Clin. Med.*, 13(Suppl):217–22 (1988).

Beattie et al., "Evidence that Modulation Requires Sequences Downstream of the Promoters of Two vir–Repressed Genes of *Bordetella pertussis*," *J. Bacteriol.*, 172/12:6997–7004 (1990).

Beattie et al., "Repressor Binding to a Regulatory Site in the DNA Coding Sequence Is Sufficient To Confer Transcriptional Regulation of the vir–Repressed Genes (vrg Genes) in *Bordetella pertussis*," *J. Bacteriol.*, 175/2:519–27 (1993)).

Beattie et al., "A vir–Repressed Gene of *Bordetella pertussis* is Required for Virulence," *Infection and Immunity*, 60/2:571–577 (1992).

Betsou et al., "CyaC–Mediated Activation is Important Not Only for Toxic but Also for Protective Activities of *Bordetella pertussis* Adenylate Cyclase–Hemolysin," *Infection and Immunity*, 61/9:3583–3589 (1993).

Brennan et al., "Identification of a 69–Kilodalton Nonfimbrial Protein as an Agglutinogen of *Bordetella pertussis*," *Infection and Immunity*, 56/12:3189–3195 (1988).

Charles et al., "Molecular cloning and characterization of protective outer membrane protein P.69 from *Bordetella pertussis*", *Proc. Natl. Acad. Sci. USA*, 86:3554–3558 (1989).

Friedman, "*Bordetella pertussis* Adenylate Cyclase: Isolation and Purification by Calmodulin–Sepharose 4B Chromatography", *Infection and Immunity*, 55/1:129–134 (1987).

Goldman et al., "Spontaneous phase variation in *Bordetella pertussis* is a multistep non–random process," *EMBO Journal*, 3/6:1353–1356 (1984).

Grimprel et al., "Long–Term Human Serum Antibody Responses after Immunization with Whole–Cell Pertussis Vaccine in France," *Clinical & Diagostic Laboratory Immunology*, 3/1:93–97 (1996).

Gross et al., "Targeted mutations that ablate either the adenylate cylase or hemolysin function of the bifunctional cyaA toxin of *Bordetella pertussis* abolish virulence," *Proc. Natl. Acad. Sci. USA*, 89:4898–4902 (1992).

Gueirard et al., Human *Bordetella bronchiseptica* Infection Related to Contact with Infected Animals: Persistence of Bacteria in Host, *J. Clin. Microbiol.*, 33/8:2002–2006 (1995).

Gueirard et al., Human *Bordetella bronchiseptica* Infection Related to Contact with Infected Animals: Persistence of Bacteria in Host, *J. Clin. Microbiol.*, 33/8:2002–2006 (1995).

Gueirard et al., "Virulence of *Bordetella bronchiseptica*: Role of Adenylate Cyclase–Hemolysin," *Infection & Immunity*, 61/10:4072–4078 (1993).

Gueirard et al., "Virulence of *Bordetella bronchiseptica*," Bacterial Protein Toxins, ed. Freer et al., Suppl. 24:152–153 (1994).

Glaser et al., "The calmodulin–sensitive adenylate cyclase of *Bordetella pertussis*: cloning and expression in *Escherichia coli*", *Molecular Microbiology* 2/1:19–30 (1988).

Guiso et al., Protective activity of Bordetella adenylate cyclase–hemolysin against bacterial colonization, *Microbial Pathogenesis*, 11:423–431 (1991).

(List continued on next page.)

*Primary Examiner*—James C. Housel
*Assistant Examiner*—V. Ryan
*Attorney, Agent, or Firm*—Finnegan, Henderson, Farabow, Garrett & Dunner, L.L.P.

[57] ABSTRACT

An immunogenic composition, characterized in that it comprises an adenyl cyclase-hemolysin (Ac-Hly) protein, or an immunogenic portion of this AC-Hly, of a strain of Bordetella chosen from *B. pertussis*, *B. parapertussis* or *B. bronchiseptica*, and in that it comprises, in addition, a bacterial extract containing the expression products of the vrg genes of a strain of Bordetella chosen from *B. pertussis*, *B. parapertussis* or *B. bronchiseptica*, or a portion of these expression products which is sufficient to induce an immune response in a host to which the extract might be administered.

3 Claims, 6 Drawing Sheets

OTHER PUBLICATIONS

Hackett et al., "Hemolytic, but Not Cell–invasive Activity, of Adenylate Cyclase Toxin is Selectively Affected by Differential Fatty–acylation in *Escherichia coli*", *The Journal of Biological Chemistry*, 270/35:20250–20253 (1995).

Hackett et al., Internal Lysine Palmitoylation in Adenylate Cyclase Toxin from *Bordetella pertussis, Science*, 226:433–435 (1994).

Hausman et al., Analysis of Proteins Encoded by the ptx and ptl Genes of *Bordetella bronchiseptica* and *Bordetella parapertussis, Infection and Immunity*, 64/10:4020–4026 (1996).

Hewlett et al., "Adenylate Cyclase Toxin from *Bordetella pertussis*: Identification and Purification of the Holotoxin Molecule", *The Journal of Biological Chemistry*, 264/32: 19379–19384 (1989).

Horiguchi et al., Effects of *Bordetella bronchiseptica* Dermonecrotic Toxin on the Structure and Function of Osteoblastic Clone MC3T3–E1 Cells, *Infection and Immunity* 59/3:1112–1116 (1991).

Iwaki et al., "Identification by in vitro complementation of regions required for cell–invasive activity of *Bordetella pertussis* adenylate cyclase toxin", *Molecular Microbiology*, 17/6:1015–1024 (1995).

Kessin et al., "Secreted Adenylate Cyclase of *Bordetella pertussis*: Calmodulin Requirements and Partial Purification of Two Forms," *Journal of Bacteriology*, 166/1:290–296 (1986).

Khelef et al., "Characterization of Murine Lung Inflammation after Infection with Parental *Bordetella pertussis* and Mutants Deficient in Adhesions or Toxins," *Infectin and Immunity*, 62/7:2893–2900 (1994).

Khelef et al., "Bordetella Species are Immunologically Different," Bacterial Protein Toxins ed. Freer et al., Suppl. 24:514–515 (1994).

Khelef et al., "Both adenylate cyclase and hemolytic activities are required by *Bordetella pertussis* to initiate infection," *Microbial Pathogenesis*, 12:227–235 (1992).

Knapp et al., "Two trans–Acting Regulatory Genes (vir and mod) Control Antigenic Modulation in *Bordetella pertussis,*" *J. Bacteriol.* 170/11:5059–5066 (1988).

Ladant et al., "*Bordetella pertussis* Adenylate Cyclase: Purification, Characterization and Radioimmunoassay," *The Journal of Biological Chemistry*, 261/34:16264–162169 (1986).

Le Blay et al., "Antigenic polymorphism of the lipopolysaccharides from human and animal isolates of *Bordetella bronchiseptica,*" *Microbiology*, 143:1433–1441 (1997).

Munoz et al., Mouse–Protecting and Histamine–Sensitizing Activities of Pertussigen and Fimbrial Hemagglutinin from *Bordetella pertussis, Infection and Immunity*,32/1:243–250 (1981).

Novotny et al., "Adenylate Cyclase Activity of a 68,000–Molecular–Weight Protein Isolated from the Outer Membrane of *Bordetella bronchiseptica,*" *Infection and Immunity*, 50/1:199–206 (1985).

Novotny et al., "Biologic and Protective Properties of the 69–kDa Outer Membrane Protein of *Bordetella pertussis*: A Novel Formulation for an Acellular Pertussis Vaccine," *Journal of Infectious Diseases*, 164:114–22 (1991).

Novotny, "Bordetella Adenylate Cyclase: A Genus Specific Protective Antigen and Virulence Factor," *Proceedings of the Fourth International Symposium on Pertussis*, Developed Biol. Standard, 61:27–41 (1985).

Passerini de Rossi et al., "Flagellin, a major protein present in SDS–Page profiles of Sarkosyl–OMP–enriched fractions from *Bordetella bronchiseptica* Bvg—or modulated Bvg+ strains," *Veterinary Microbiology*, 56:65–77 (1997).

Pittman, "Pertussis Toxin: The Cause of the Harmful Effects and Prolonged Immunity of Whooping Cough. A Hypothesis," *Reviews of Infectious Diseases*, 1/3:401–412 (1979).

Shattuck et al., "Purification and Characterization of a Calmodulin–Sensitive Adenylate Cyclase from *Bordetella pertussis,*" *Biochemistry*, 24:6356–6362 (1985).

Beattie et al. Journal of Bacteriology 172(12):6997–7004, 1990.

Beattie et al. Infection and Immunity 60(2):571–577, 1992.

Beattie et al. Journal of Bacteriology 175(2):519–527, 1993.

Knapp et al. Journal of Bacteriology 170(11):5059–5066, 1988.

BORDETELLA PERTUSSIS AND BORDETELLA PARAPERTUSSIS STRAINS

This is a continuation of application Ser. No. 08/591,799, filed Jan. 25, 1996, which is a continuation of application Ser. No. 08/574,439, filed Dec. 15, 1995. Prior applications Ser. Nos. 08/591,799 and 08/574,439 are hereby incorporated in their entireties herein by reference.

BACKGROUND OF THE INVENTION

The genus Bordetella comprises four species *Bordetella pertussis, Bordetella parapertussis, Bordetella bronchiseptica* and *Bordetella avium.*

The bordetellae are Gram-negative coccobacilli responsible for respiratory infections. *Bordetella pertussis* and *Bordetella parapertussis,* agents of whooping cough, are strictly human pathogens. *Bordetella bronchiseptica* is pathogenic for various mammals, and more rarely for man, and, in distinction to *B. pertussis* and *B. parapertussis,* is capable of surviving outside the host. Bordetella avium is pathogenic only for birds.

Since the introduction of whooping cough vaccination in countries where vaccine cover is greater than 80%, it has been possible to observe a dramatic fall in morbidity and mortality. This fall is indeed attributable to vaccination since, in several countries (Great Britain, Sweden, Japan, etc.), deadly epidemics of whooping cough have taken place in the years following the cessation of vaccination.

The invention affords immunogenic compositions which can participate in the making of whooping cough vaccines, these compositions being at least partly of the "acellular" type and displaying an efficacy at least identical to that of the known vaccine.

The invention relates, on the one hand to vaccines which can be used in veterinary medicine, and on the other hand to vaccines which can be used in human medicine.

The whooping cough vaccine in current use is a cellular vaccine composed of heat-inactivated bacterial suspensions of *B. pertussis* (mixture of two strains differing in the expression of agglutinogens). This vaccine is generally used in combined form with purified diphtheria and tetanus fractions, the hemophilus and the inactivated polio viral component. Vaccination consists of three injections at one-month intervals from the age of two months and an injection at 18 months. No other booster injection is performed thereafter.

This vaccine is sometimes poorly tolerated, both locally and generally. It has, in particular, been blamed for giving rise to serious neurological complications of the acute encephalitis type; however, very recent studies appear to conclude that there is no statistical proof of a relationship between the cellular vaccine and the severe neurological complications (Griffiths A. H. Vaccine 1989; 7:199–210).

It remains nonetheless true that the cellular vaccine is poorly tolerated and is responsible for reversible, but undesirable, effects. For these reasons, a new vaccine lacking these effects is desirable. In order to envisage the defining of a new vaccine, it appeared necessary to characterize certain factors involved in the virulence of the bacterium and, where appropriate, in the regulation of the virulence. When purified, each and every one of these different factors is a theoretical candidate for the making of a whooping cough vaccine termed "acellular" as opposed to the traditional vaccine. This new type of vaccine should provide, in addition to better tolerance, an efficacy at least equal to that of the traditional vaccine.

The factors involved in the virulence of *B. pertussis* have been identified as follows: whooping cough may be defined in broad outline by the association of an infections syndrome, involving the adhesion of the bacteria to the target cells (ciliated cells of the respiratory apparatus), without invasion or dissemination in the host's body, and of a secondary toxin-induced syndrome including the local cytopathogenic effects which are elective for the ciliated respiratory epithelium (destruction and removal of ciliated cells, accumulation of mucus, inflammatory reaction) and systemic effects, the most obvious of which is hyperleucocytosis with hyperlymphocytosis.

As a result of recent techniques in molecular biology, a number of factors involved in the virulence of *B. pertussis* have been characterized and the regulation of their expression understood. These factors may be classified in two categories, those participating in the infectious syndrome (adhesins) and those playing a part in the toxin-induced syndrome (toxins).

The adhesins:

filamentous hemagglutinin or FHA is considered to play a major part in the adhesion of the bacterium to the ciliated epithelium (Locht C., Bertin P., Menozzi F. D. and Renaud G. Mol. Microbiol. 1993, 9:653–66). FHA is always expressed by the virulent strains and is secreted. Its structural gene has been cloned and sequenced (Relman D. et al., 1989, Proc. Natl. Acad. Sci. USA, 86:2637–2641). It codes for a protein of 360 kDa, but only a 220-kDa fragment can be purified. This protein binds to the glycoproteins of ciliated cells and possesses binding sites for the integrins of lymphocytes and macrophages. It has just been shown recently that FHA displays a homology with certain proteins of the host's endothelial cells (Tuomanen E., Prasad S. M., George J. S., Hoepelman A. I. M., Ibsen P., Heron I., and Starzyk R. M. 1993. Proc. Natl. Sci. USA. 90:7824–7828).

The two agglutinogens or AGGs of *B. pertussis* enable strains to be classified in serotypes. Two AGGs have been characterized. These proteins are secreted and play a part in the adhesion of the bacterium to the epithelial cells (Mooi F. Van der Heide H. G. D., Ter Avest A. R., Welinder K. G., Livey I., Van der Zeijst B. A. M., and Gaastra, W. 1987. Microb. Pathog. 2:473–484).

Pertactin or PRN is a protein of 93 kDa, but only a 69-kDa fragment can be purified. This protein possesses two binding sites for the integrins of macrophages and of lymphocytes (Charles I, Dougan G., Pickard D., Chattfield S. Smith M. Novotny P., Morissey P. and Fairweather N. F. 1989 Proc Natl Acad Sci. 86:3554–3558).

Pertussis toxin or PTX, a secreted type A-B toxin which, besides its cytopathogenic effects, participates in adhesion via its B subunit. The B oligomer is capable of binding to the receptors of ciliated cells, but not necessarily to the same receptors as those for FHA. The binding of PTX to leukocytes would appear to prevent their migration to the site of the inflammatory reaction. This binding appears to induce an increase in the number of functional integrin molecules to leukocytes, thereby promoting binding of the bacterium via FHA (Rozindski E., Burnette W. N., Jones T., Mar V., and Tuomanen E. 1993 J. Exp. Med. 178:917–924).

The Toxins:

Pertussis toxin or PTX is secreted and considered to be the major toxin of *B. pertussis*. Its A subunit possesses ADP-ribosyl transferase activity. After binding of the B portion of the toxin to the target cell, this A subunit is capable of entering the cell, of inactivating the regulatory G proteins and thus of causing interference with all cellular functions. It is this factor which appears to be responsible for the generalized biological effects observed during the disease, such as hyperlymphocytosis, hyperinsulinemia and sensitivity to histamine.

Dermonecrotic toxin or DNT, which has not yet been well characterized, and tracheal cytotoxin or TCT, a secreted small glycoprotein of the muramyl peptide family, derived from the peptidoglycan of the bacterium, appear to act in concert to destroy the ciliated cells of the host's respiratory apparatus. TCT prevents, in addition, the regeneration of the respiratory epithelium (Luker K., Collier J. L., Kolodziej E. W., Marshall G. R., and Goldman W. E. 1993. Proc. Natl. Acad. Sci. USA. 90:2365–2369).

Adenyl cyclase-hemolysin or Ac-Hly is a bifunctional protein possessing adenyl cyclase activity and hemolytic activity. It is secreted by the bacterium. Its structural gene has been cloned and sequenced (Glaser P. et al., 1988, Molec. Microb. 2, 19–20). This protein has been found to belong to the family of toxins termed "RTX" for "repeats in toxins", and displays homologies with the hemolysin or *Escherichia coli* and of *Actinobacillus pleuropneumoniae* and the leukotoxins of *Pasteurella haemolytica* and of *Actinobacillus actinomycetemcomitans*. This protein, like PTX, is capable of entering eukaryotic cells such as macrophages, of being activated by calmodulin, of synthesizing large amounts of cAMP and of intefering with the cellular functions (Coote J. 1992. FEMS Microbiol. Rev. 88:137–162).

Similarly, the factors involved in the virulence of *B. parapertussis* and *B. bronchiseptica* have been identified.

*B. pertussis, B. parapertussis* and *B. bronchiseptica* infections are indistinguishable from a clinical standpoint. These bacteria have more than 75% homology in respect of the DNA. They have been classified in species only on the basis of phenotypic and biochemical characters. *B. parapertussis* and *B. bronchiseptica* synthesize virulence factors functionally and immunologically very close to *B. pertussis,* with the exception of PTX.

A vaccine composed of bacterial suspensions of inactivated *B. pertussis* protects against a *B. pertussis* infection, but also against a *B. parapertussis* and a *B. bronchiseptica* infection in the mouse model. Although there are no epidemiological data on *B. parapertussis* infections in France, it should be noted that few strains of this species are isolated in this country, a country which has been vaccinated for 25 years with a "pertussis vaccine", whereas they are isolated in unvaccinated or poorly vaccinated countries.

Besides the presence of these different adhesins and toxins, the bordetellae are characterized by a regulation of the expression of the factors involved in their virulence. In other words, the bordetellae undergo phase variations and modulations.

The bordetellae, depending on their environment, may become "avirulent", that is to say incapable of inducing lethality, an inflammatory reaction and pulmonary lesions in the mouse model of respiratory infection. They undergo either a phase modulation or a phase variation. The phase variation is observed at a frequency ranging from $10^{-3}$ to $10^{-6}$ and is almost irreversible. It manifests itself in a cessation of the expression of the toxins and adhesins described above and in the expression of other factors which have not yet been well characterized (change of Phase I "virulent" bacteria to Phase IV "avirulent" bacteria). The Phase I and Phase IV bacteria have been described by Lacey B. 1960, J. Hyg. 58:57–93. The phase modulation, phenotypically similar to the phase variation, is completely reversible and manifests itself in a cessation of the synthesis of the adhesins and the toxins when there are environmental changes (composition of the culture medium, temperature, etc.).

The phase variation and phase modulation observed in Bordetella are under the control of two regulatory genes bvg A and bvg S (Arico B. et al., 1989, Proc. Natl. Acad. Sci USA 86:6671–6675).

The bvg S gene codes for a protein sensitive to external conditions. This protein modulates by phosphorylation the activity of the protein encoded by the bvgA gene, which is, on the one hand a positive activator of the transcription of the genes coding for the virulence factors (vag genes for "vir activated genes ") mentioned above (Uhl M. A. and Miller J. 1994. Proc. Natl. Acad. Sci USA 91:1163–1167), and on the other hand a repressor of the transcription of certain genes (Beattie D. T. et al., J. of Bacteriology, Jan 93, p. 159–527). The genes whose expression is repressed are referred to as vrg genes for "vir repressed genes", and are still poorly characterized. It has, however, been shown that the vrg 6 gene of *B. pertussis* codes for a protein having a role in the peristance of the bacterium in the host (Beatties D. et al., 1992, Infect. Imm. 60:571–577). In *B. bronchiseptica,* two proteins encoded by the vrg genes have been characterized: they are proteins of the flagella type (Phase I *B. bronchiseptica* is an immobile bacterium which does not synthesize flagella but synthesizes adhesins and toxins, and Phase IV *B. bronchiseptica* is a mobile bacterium which synthesizes flagella).

In order to measure the virulence of the bacteria and to evaluate the local and general toxinic effects, a mouse model of respiratory infections has been developed (Guiso N. et al., 1991, Microb. Pathogen 11, 423–431). Using this mouse model, it has been possible to show that chemically or genetically inactivated PTX is a good immunogen. This anatoxin has a protective activity against lethal *B. pertussis* infections, but does not appear to induce the synthesis of effective antibodies against the persistance of the bacterium (Khelef. N. Danve B. Quentin-Millet M. J. and Guiso N. 1993 Infect Immun. 64:486–490).

These results relating to the virulence of bordetellae and to the regulation of this virulence show that whooping cough is a multifactorial disease and that the vaccine must not only protect against lethal infections but also against the persistance of the bacterium. Similar conclusions apply to the infections due to *B. parapertussis* or to *B. bronchiseptica.*

Attempts to develop an acellular vaccine from the isolated components of the adhesin or toxin family have been performed. Thus, acellular compositions containing either purified *B. pertussis* toxin (PTX) or this toxin combined with purified filamentous hemagglutinin (FHA) have been prepared.

The first trials of tolerance of these acellular compositions (PTX or PTX-FHA) in man show a marked decrease in both local complications (pain, swelling) and general complications (fever, convulsions, etc.) in comparison with the traditional cellular vaccine (Edward K., J. Infect. Dis. 1993, 168, 15–20).

These new preparations (PTX or PTX-FHA) have good immunogenicity and induce a high level of antibodies. However, the test for vaccinal antibodies is an imperfect method, since seroconversion is not synonymous with protection against the disease, and no demonstration has been made of the protective character of the antibodies obtained, or of the possible level of protection.

The results of clinical trials of different cellular and acellular vaccines have been published (International Symposium on Pertussis Vaccine trials, Rome 30.10.95-1.11.95). These results show that not all the cellular vaccines are equivalent, some are very effective and induce few side effects and others are of very low efficacy and induce greater side effects.

The published results show that the acellular vaccines tested, monovalent (PTX), bivalent (PTX, FHA), trivalent (PTX, FHA, PRN) or pentavalent (PTX, FHA, PRN, AGG2, AGG3) induce very few side effects, are all immunogenic and all have an efficacy against the disease (according to WHO definition) which is greater than or equal to 70%. However, the efficacy of an acellular PTX-FHA vaccine is always less, irrespective of the particular definition which may be used, than that of an effective cellular vaccine.

In spite of the encouraging results obtained as regards the immunogenicity of different compositions containing both adhesins and toxins of B. pertussis, the inventors considered that an effective protection against the disease due to B. pertussis, B. parapertussis or B. bronchiseptica infection necessitated consideration of additional factors with respect to the adhesins and toxins, and especially factors participating in the persistance of the bacterium.

Their observations led them to define a model described in detail in the experimental part, from which new criteria prior to the definition of vaccines have been defined.

Thus, according to the present application, to define effective and substantially nontoxic vaccines against at least one of the bordetellae B. pertussis, B. parapertussis or B. bronchiseptica, it is appropriate to employ not only one or more adhesins and/or toxins of these bacteria, but also one or more factors whose synthesis is repressed when there is expression of the toxins and adhesins of the bacterium. These factors are, in particular, expression products of the vrg genes which have been referred to above.

SUMMARY OF THE INVENTION

With the object of preparing a whooping cough vaccine lacking side effects and which is protective against the local or systemic effects due to the toxins synthesized by B. pertussis and/or B. parapertussis and/or B. bronchiseptica, and protective against the persistance of these bacteria in the host, the subject of the invention is an immunogenic composition, characterized in that it comprises an adenyl cyclase-hemolysin (AC-Hly) protein, or an immunogenic portion of this AC-Hly, characteristic of a strain of Bordetella chosen from B. pertussis, B. parapertussis or B. bronchiseptica, and in that is comprises, in addition, a bacterial extract containing the products of the vrg genes of a strain of Bordetella chosen from B. pertussis, B. parapertussis or B. bronchiseptica, or a portion of these expression products which is sufficient to induce an immune response in a host to which the extract might be administered.

None of the acellular vaccines prepared to date contains AC-Hly. Now, according to the inventors, this protein should be incorporated in a vaccinating composition since it plays an important part in the virulence of the bordetellae for the following reasons:

it is expressed very early after infection, since specific antibodies are synthesized and detected, both in infected humans and in infects animals, from the beginning of the infection (Khelef N., Sakamoto H., and Guiso N. 1992. Microbiol. Pathogen. 12:227–235 and Gueirad P. and Guiso N. 1993 Infect. Immun. 61:4072–4078).

it is necessary to the bacterium in order to initiate infection (Khelef N. Sakamoto H. and Guiso N. 1992 Microbiol. Pathogen. 12:227–235).

its use in purified form as antigen in the mouse model of respiratory infection protects the mice against colonization of the respiratory apparatus (Guiso, Szatanik and Rocancourt. 1989 Microb. Pathogen. 11:423–431).

it is responsible in vitro for the death of alveolar macrophages by apoptosis (Khelef, Zyglinski and Guiso Infect. Immun. 61:4064–4071). The other adhesins or toxins do not participate in the apoptosis process.

Moreover, the presence in the immunogenic composition of a bacterial extract comprising the expression products of the vrg genes would enable the humoral and/or cellular immune response obtained after infection to be improved in vaccinated subjects and would also contribute to the protection against the persistance of the bacterium.

The bacterial extract termed "vrg bacterial extract", which has been referred to above, contains all the constituents of the outer membrane, including the LPS endotoxin, of a phase IV bacterium, that is to say of a bacterium not expressing the VAG genes. The LPS endotoxin may alternatively be removed or detoxified.

This extract may be present in suspension form.

DESCRIPTION OF PREFERRED EMBODIMENTS

A first preferred immunogenic composition of the invention is an immunogenic composition which is characterized in that it comprises, in addition, one or more adhesins or toxins, respectively, or B. pertussis, B. parapertussis or B. bronchiseptica, chosen from FHA, the AGGs or PRN and PTX.

The adhesins of the bordetellae strengthen the immunogenic character of the composition containing AC-Hly and the vrg bacterial extract.

According to a first embodiment of the invention, the immunogenic composition is characterized in that it comprises the PTX toxin of B. pertussis, the AC-Hly toxin of B. pertussis, and the FHA and PRN adhesins, and a bacterial extract containing the proteins encoded by the vrg genes of B. pertussis, or a portion of these proteins which is sufficient to induce an immune response in a host to which the extract might be administered.

Such a composition may be employed for preparing vaccines which are protective against the lethal and systemic effects of B. pertussis in man and against the persistance of the bacterium.

According to a preferred embodiment of the invention, the AC-Hly toxin of B. pertussis is also contained in a bacterial extract containing all or part of the virulence factors of the adhesin or toxin group of B. pertussis.

The "vag" or "vrg" bacterial extracts which are employed for implementing the invention are preferably extracts termed "urea extracts".

A "urea extract" is composed of a mixture of proteins expressed at the surface of the bacterium and which are separated from the bacterium after incubation of the latter with 5M urea. The "vag urea extract" of B. bronchiseptica, for example, contains, among other proteins, AC-Hly, FHa, PRN and LPS (lipopolysaccharide endotoxin), and the "vrg urea extract" contains several proteins not yet characterized, the flagella and LPS.

The use of urea extracts makes it possible, in particular, to produce a vaccine which is cheaper compared to a vaccine which would be obtained from the proteins contained in the extracts, in purified form.

In addition, the inventors found that the urea extracts used can induce a T type cellular immune response (lymphoproliferation), thus behaving like the cellular vaccine used hitherto.

On the contrary, exclusively acellular compositions would not induce a T response, which reaction, however, occurs in the case of infection.

The vag or vrg urea extracts are prepared, respectively, from phase I or phase IV bacteria. Where appropriate, the phase IV bacteria are replaced by bacteria whose bvgS gene is mutated in such a way that the bacteria express only the proteins encoded by the vrg genes.

The preparation of these extracts is described in detail in the experimental part.

Thus the invention relates preferentially to an immunogenic composition comprising both a vag urea extract of B. pertussis and a vrg urea extract of B. pertussis.

A B. pertussis strain which is suitable for the preparation of these extracts is the strain HAV falling within the scope of the invention and deposited at the CNCM (Collection Nationale de Cultures de Microorganismes [National Collection of Microorganism Cultures] in Paris) on Oct. 19, 1994 under No. I-1485. To prepare the vag urea extract, the strain HAV may be used directly since it is a phase I strain.

In contrast, the vrg urea extract is obtained from a phase IV strain derived from the phase I strain, for example by mutation of the bvgS gene of the bacterium or by culturing said phase I strain in a medium containing only magnesium sulfate so as to obtain the expression of only the vrg genes of B. pertussis.

The invention affords, in addition, immunogenic compositions prepared, according to the principles described above for B. pertussis, from the bordetellae of the B. parapertussis or B. bronchiseptica family.

It is, in effect, known that vaccination with the cellular vaccine available on the market, that is to say composed of bacterial suspensions of inactivated phase I B. pertussis bacteria, protects against B. pertussis and B. parapertussis infections in the mouse model. However, it has recently been demonstrated that administration of the purified B. pertussis factors (PTX or FHA or PRN) does not protect against the disease and the infection due to B. parapertussis. Similarly, the administration of the purified AC-Hly of B. parapertussis does not protect against a B. pertussis infection in the mouse model.

These results suggest that, in spite of a very high homology between the two species, the protection is species-specific. Hence the use of acellular vaccines composed of PTX, PRN and FHA of B. pertussis strains alone as whooping cough vaccines in years to come would incur the risk of causing an increase in B. parapertussis infection (Khelef Danve Quentin-Millet and Guiso 1993, Infect. Immun. 61:46–490 and Gueirad P., and Guiso 1993 Infect. Immun 61:4072–4078).

Hence the invention also affords immunogenic compositions which are characterized in that they comprise the AC-Hly toxin of B. parapertussis and a bacterial extract containing all or part of the proteins encoded by the vrg genes of B. parapertussis.

Advantageously the AC-Hly toxin of B. parapertussis is contained in a bacterial extract containing all or part of the virulence factors of the adhesin or toxin group of B. parapertussis. Such an extract is preferably a vag urea extract obtained, for example, from B. parapertussis strain No. 1 deposited at the CNCM on Dec. 2, 1994 under No. I-1498. B. parapertussis strain No. I-1498 falls within the scope of the present invention.

Similarly the vrg bacterial extract is preferably a vrg urea extract obtained, for example, from B. parapertussis strain No. 1, deposited at the CNCM on Dec. 2, 1994 under No. I-1498, according to procedures similar to those which have been described for the B. pertussis strain.

According to another aspect, and especially with the object of producing a veterinary vaccine, the present application affords immunogenic compositions which are characterized in that they comprise the AC-Hly toxin of B. bronchiseptica and a bacterial extract containing all or part of the proteins encoded by the vrg genes of B. bronchiseptica.

As mentioned above in connection with B. pertussis and B. parapertussis, the AC-Hly toxin of B. bronchiseptica is contained in a bacterial extract comprising all or part of the virulence factors (adhesins and/or toxins) of B. bronchiseptica.

The extract in question is advantageously a vag urea extract obtained, for example, from B. bronchiseptica strain 973S deposited at the CNCM on May 12, 1989 under No. I-858.

Similarly, the vrg urea extract is preferably obtained from B. bronchiseptica strain 973S, deposited at the CNCM on May 12, 1989 under No. I-858, according to the procedures described above for B. pertussis.

According to another particular embodiment of the invention, an immunogenic composition as described above which is capable of inducing the production of antibodies against B. bronchiseptica comprises polypeptide components characteristic of the flagella of B. bronchiseptica. These components have been described by Akerley B. J. et al. (J. of Bact. Feb 1992, p. 980–990).

Antibordetella humoral immunity has been considered for a long time to be the only important one. In effect, it has been known for a very long time that, after infection, anti-PTX and anti-FHA antibodies may be detected in the serum of patients. Furthermore, it is possible to protect passively against the disease, in the mouse model, with anti-PTX antibodies. The circulating antibodies hence play a part in the neutralization of PTX and in the inhibition of the attachment of the bacterium.

However, a correlation has never been demonstrated between the level of antibodies specific for these antigens in the serum of vaccinated or infected individuals and protection against the disease. Very little is known regarding the immunity of the other factors, especially AC-Hly, PRN and LPS. It has, however, been shown that it is possible to protect mice passively against a B. pertussis infection with anti-AC-Hly antibodies.

that, in the serum of unvaccinated infected children (above 8 months of age in order to avoid the presence of material antibodies which may distort the interpretation of the serology, and below two years of age in order to know the clinical history) or sera of mice infected with clinical isolates of B. pertussis or of B. bronchiseptica, it is possible to detect anti-AC-Hly antibodies, very early, indicating that this protein is expressed in vivo and from the beginning of the infection, anti-FHA antibodies, anti-PTX antibodies and anti-LPS antibodies. Anti-PRN antibodies appear much later and do not persist for very long (Guiso, Grimprel, Anjak and Bégué 1993, Eur. J. Clin. Microbiol. Infect. Dis. 12:596–600).

Vaccination with the cellular vaccine also induces the synthesis of antibodies against these factors, whereas the acellular vaccines tested to date induce antibodies only against the factors of which they are composed.

Various studies suggest, in addition, that cellular immunity is also required for protection against infection. Several teams have shown that bordetellae can enter different cell types, epithelial cells, lymphocytes and monocytes, and can persist therein in vitro. Moreover, following epidemiological studies, it has been observed that *B. bronchiseptica* can persist for a very long time in man. Lastly, although it is not possible to isolate bacteria more than 40 days after infection in the lungs in mice, it is still possible to detect DNA by PCR. These results collectively suggest that bordetellae might persist intracellularly in the host at a given instant in the infection, and that cellular immunity might be required in order to control an intracellular state which would thus enable the bacteria to evade the host's immune defences.

The demonstration of T cell involvement during infection has been obtained recently (Redhead, Watkins, Barnard and Mills 1993, Infect. Immun. 61:3190–3298). In effect, at a sublethal does, normal mice eliminate the bacteria in 30 to 40 days, whereas T cell-deficient mice ("nude" mice) are incapable of eliminating the bacteria and develop a chronic infection. The transfer of T cells from convalescent mice to "nude" mice renders the latter capable of eliminating the bacteria. Furthermore, the spleen cells of convalescent mice produce high levels of IL-2, IFN-γ and TNF, but not of IL-4 and IL-5. This profile is characteristic of the T-cell subpopulations which are the Th1 type cells. The immunization of mice with the whole vaccine also induces a Th1 type response and a moderate antibody response, whereas immunization with an acellular vaccine composed of PTX, FHA and PRN induces a Th2 type response and a very high level of antibodies. While there is a strong correlation between high levels of serum IgG specific for *B. pertussis* antigens and an elimination of the bacterium from the lungs, direct cellular responses are, however, necessary for a complete elimination of the bacterium. The slower elimination of the bacteria in mice immunized with acellular vaccines than with whole vaccines which has been observed hence appears to be due to the fact that the acellular vaccine does not promote the induction of Th1 cells. Irrespective of the mechanism of action of Th1, it is hence now clear that the T cells play an important part, not only indirectly in stimulating antibody synthesis, but also directly in anti-*B. pertussis* immunity via the recruitment, stimulation and activation of phagocytic cells such as macrophages and neutrophilic polymorphonuclear leukocytes.

It has, in addition, been observed that bordetellae can persist in man, especially *B. bronchiseptica*. In some cases, the bacterium persists for several weeks, in others several months. During some infections, the isolates have a different appearance. This different appearance corresponds to the cessation either of AC-Hly synthesis, or of the synthesis of all the factors encoded by the vag genes.

The inventors observed, most advantageously in the context of the search for an effective protection against the disease caused by an infection due to bordetellae and against the persistance of these bacteria in the host, that the bacterial extracts according to the invention cause a humoral immune response and a cellular immune response.

They showed that, after infection with *B. bronchiseptica*, there is induction of a humoral immunity and of a cellular immunity, as in the case of a *B. pertussis* infection. Furthermore, after vaccination with purified AC-Hly, there is induction of a humoral and cellular type immunity similar to that induced after infection or reinfection.

The subject of the invention is also vaccinating compositions comprising as active principle an immunogenic composition corresponding to one of the definitions given on the foregoing pages, in combination with a pharmaceutically acceptable vehicle and, where appropriate, with an adjuvant.

Like the whooping cough vaccines currently available on the market, the vaccine according to the invention may be combined with other vaccinating active principles, for example those of the vaccine against diphtheria, polio or diseases caused by Haemophilus or, generally speaking, with any immunogenic constituent, for example a particular inactivated pathogenic agent or toxin.

A vaccinating composition according to the invention can be species-specific and consequently capable of inducing protection against *B. pertussis* or *B. parapertussis* or *B. bronchiseptica*. On the contrary, it can be a mixture comprising as active principle an immunogenic composition against *B. pertussis*, as defined above, and an immunogenic composition against *B. parapertussis*.

According to another embodiment of the invention, the vaccinating composition contains the immunogenic compositions prepared according to the invention against *B. pertussis* and against *B. parapertussis* and against *B. bronchiseptica*.

An especially preferred vaccine against *B. pertussis* is characterized in that it comprises as active principle a "vag urea extract" of *B. pertussis* and a "vrg urea extract" of *B. pertussis*, the *B. pertussis* strain used to prepare these extracts preferably being the strain HAV deposited at the CNCM under No. I-1485.

An especially preferred vaccine against *B. parapertussis* is characterized in that it comprises as active principle a "vag urea extract" of *B. parapertussis* and a "vrg urea extract" of *B. parapertussis*, the *B. parapertussis* strain used to prepare these extracts preferably being the strain No. 1 deposited at the CNCM under No. I-1498.

An especially preferred vaccine against *B. bronchiseptica* is characterized in that it comprises as active principle a "vag urea extract" of *B. bronchiseptica* and a "vrg urea extract" of *B. bronchiseptica*, the *B. bronchiseptica* strain used to prepare these extracts preferably being the strain 973S deposited at the CNCM under No. I-858.

Any vaccinating composition comprising a mixture of the vag urea extracts and the vrg urea extracts of *B. pertussis* and/or of *B. parapertussis* and/or of *B. bronchiseptica* also falls within the scope of the invention.

Where appropriate, the vag and vrg urea extracts employed are prepared from several isolates of the Bordetella species used.

The invention also affords a vaccine comprising as active principle *B. pertussis* strains expressing the vag genes and *B. pertussis* strains expressing the vrg genes, and/or *B. parapertussis* strains expressing the vag genes and *B. parapertussis* strains expressing the vrg genes, and/or *B. bronchiseptica* strains expressing the vag genes and *B. bronchiseptica* strains expressing the vrg genes.

The invention also relates to the bacterial extracts of the "urea extracts" type as are obtained by carrying out the method described in detail in the experimental part.

Immunogenic compositions or vaccinating compositions in which AC-Hly is present in pure form, or in which it is replaced by a polypeptide comprising its C-terminal portion and/or a polypeptide comprising its internal portion, also fall within the scope of the invention.

The AC-Hly may be isolated from Bordetella or prepared, for example, by genetic engineering techniques.

The subject of the invention is also antibodies as are produced in a host to which immunogenic or vaccinating compositions as are described above, or a bacterial extract, have/has previously been administered.

EXPERIMENTAL PART

On the basis of the collective results described above, the following model is proposed to explain the fate of Bordetella in the host:

Step 1. To initiate infection, the bacterium appears to express the vag genes, the adhesins such as FHA, the AGGs and PRN, thereby enabling the bacterium to adhere to the target cells, and the toxins such as AC-Hly and PTX, thereby enabling host's first line of defence to be destroyed.

Step 2. Since the aim of the bacterium is to persist and not to kill the host, it cannot continue to synthesize continuously toxins such as AC-Hly or PTX which destroy the host's defences, especially macrophages and lymphocytes. Hence it appears to stop the synthesis of its toxins but to continue synthesizing its adhesins.

Figure 1:
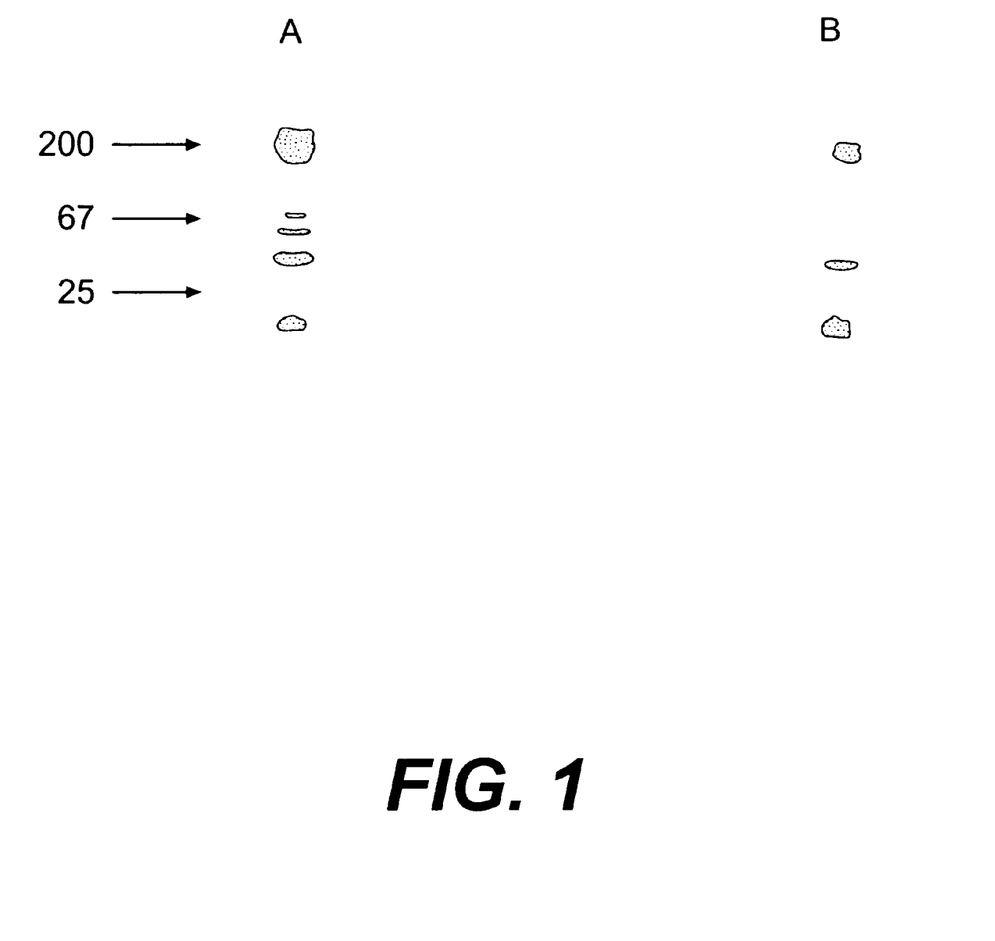
FIG. 1: Detection of specific serum antibodies after immunization with a *Bordetella bronchiseptica* vag urea extract, inactivated or otherwise.
Figure 2:
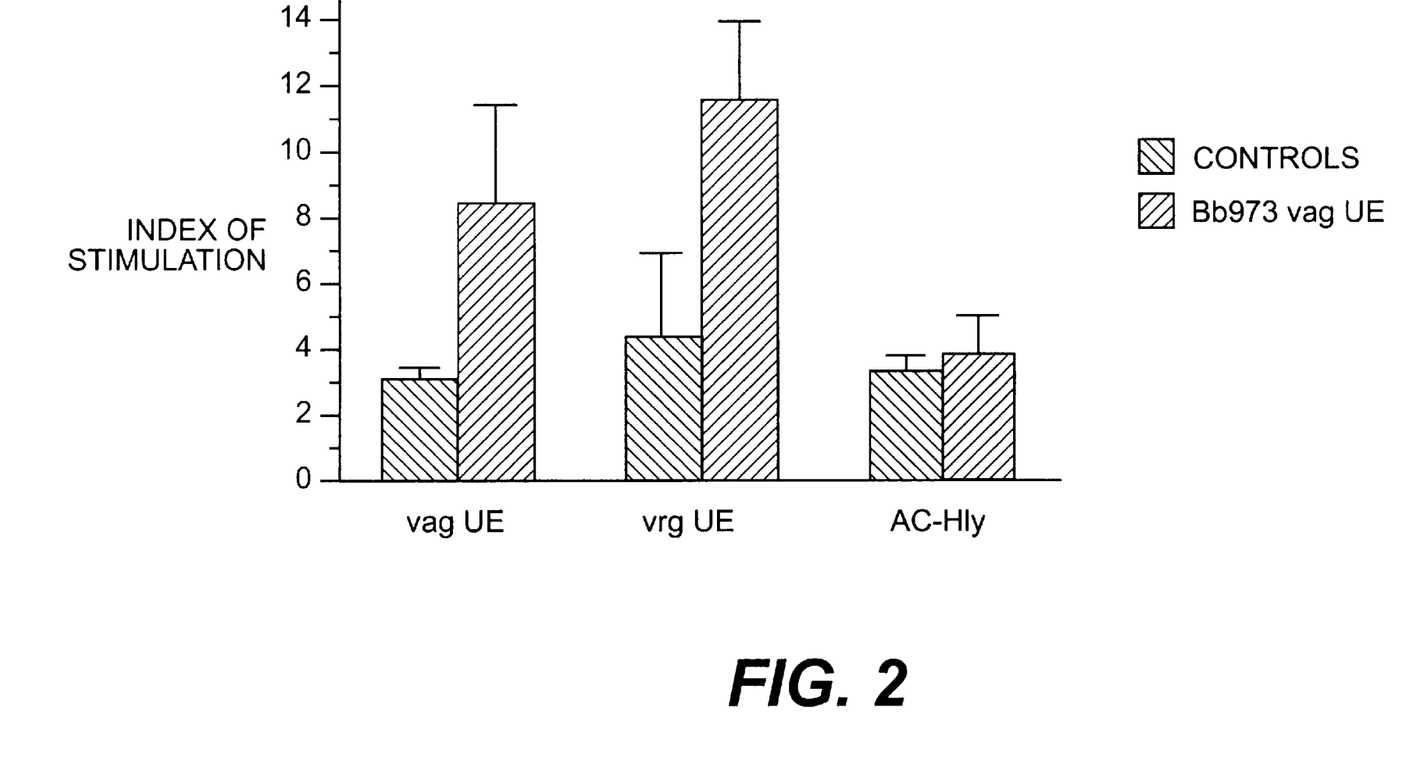
FIG. 2: Lymphoproliferation: *Bordetta bronchiseptica* vag urea extract vaccine.
Figure 3:
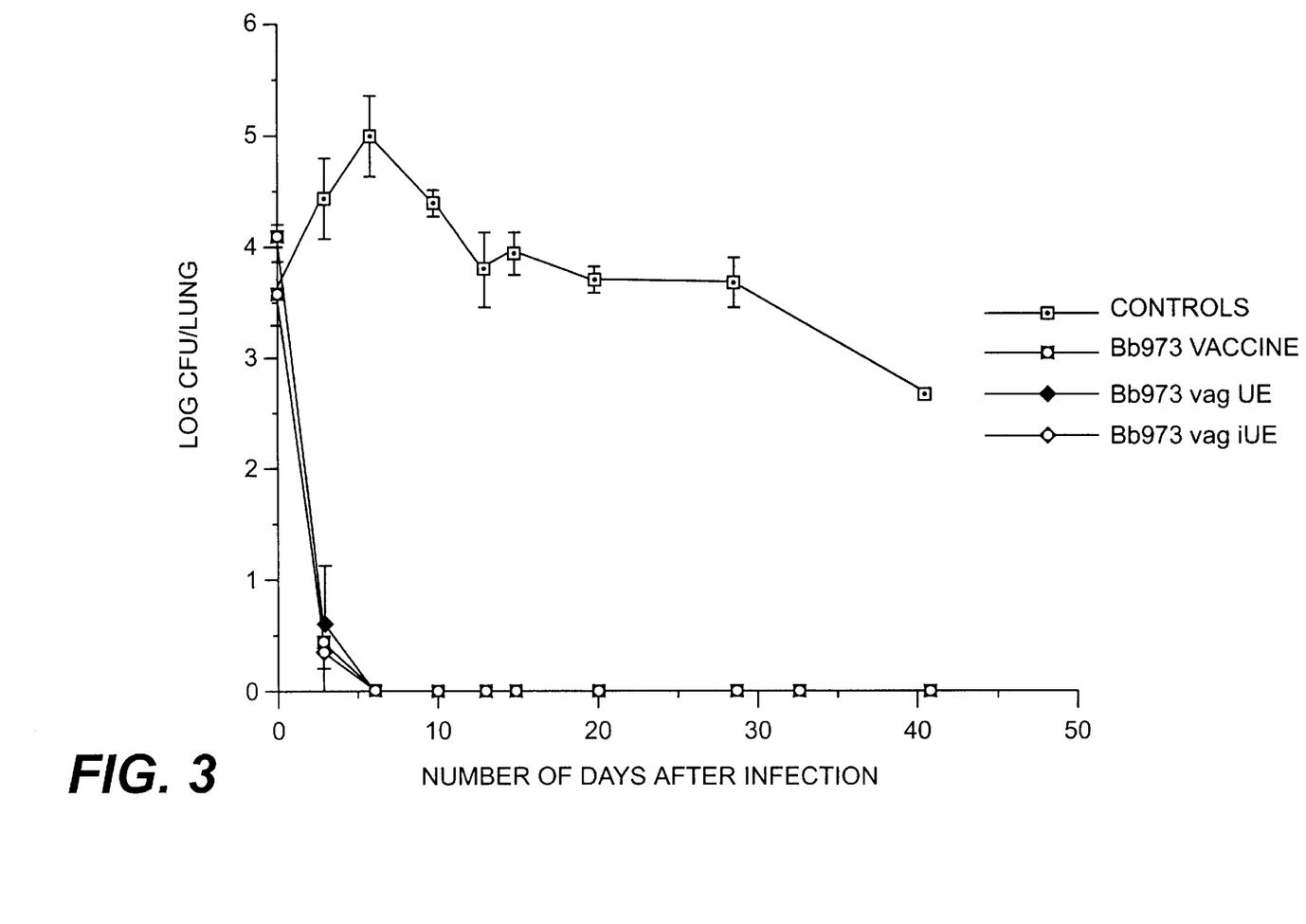
FIG. 3: Respiratory infection with *Bordetella bronchiseptica*.
Figure 4A:
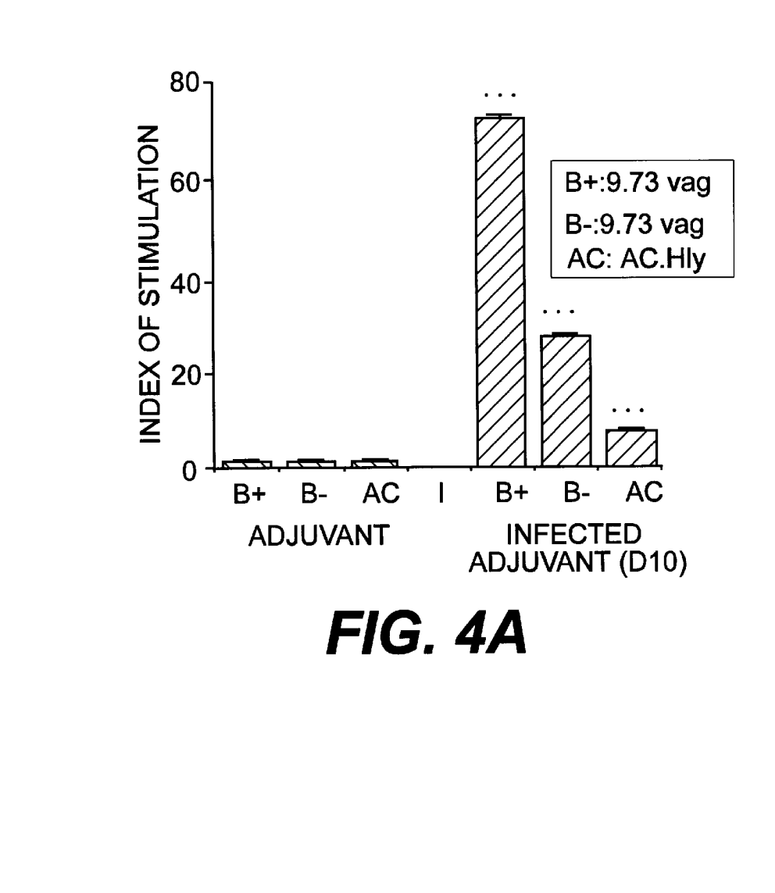
FIG. 4: Course of *B. bronchiseptica* infection and reinfection in mice exposed to primary infection with these bacteria or vaccinated with these bacteria or with purified AC-Hly.
Figure 4B:
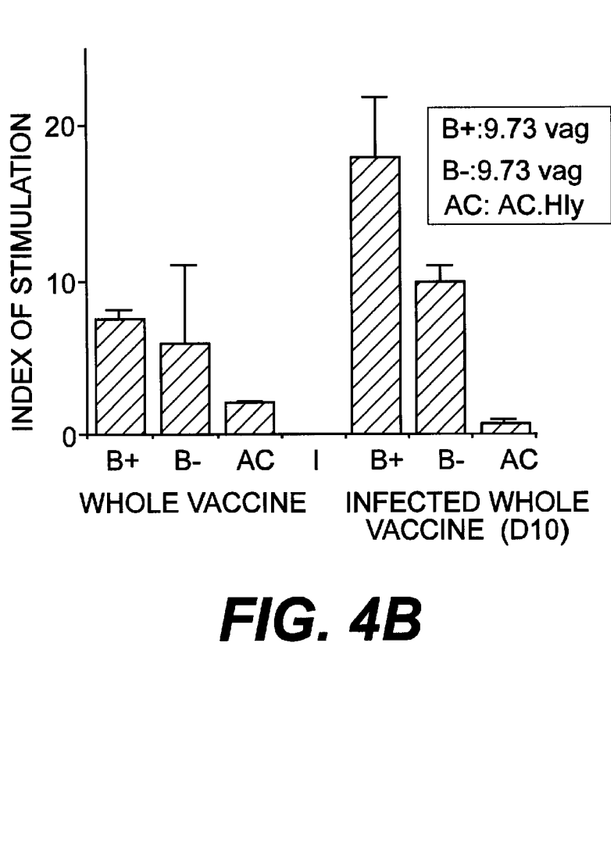
Figure 4C:
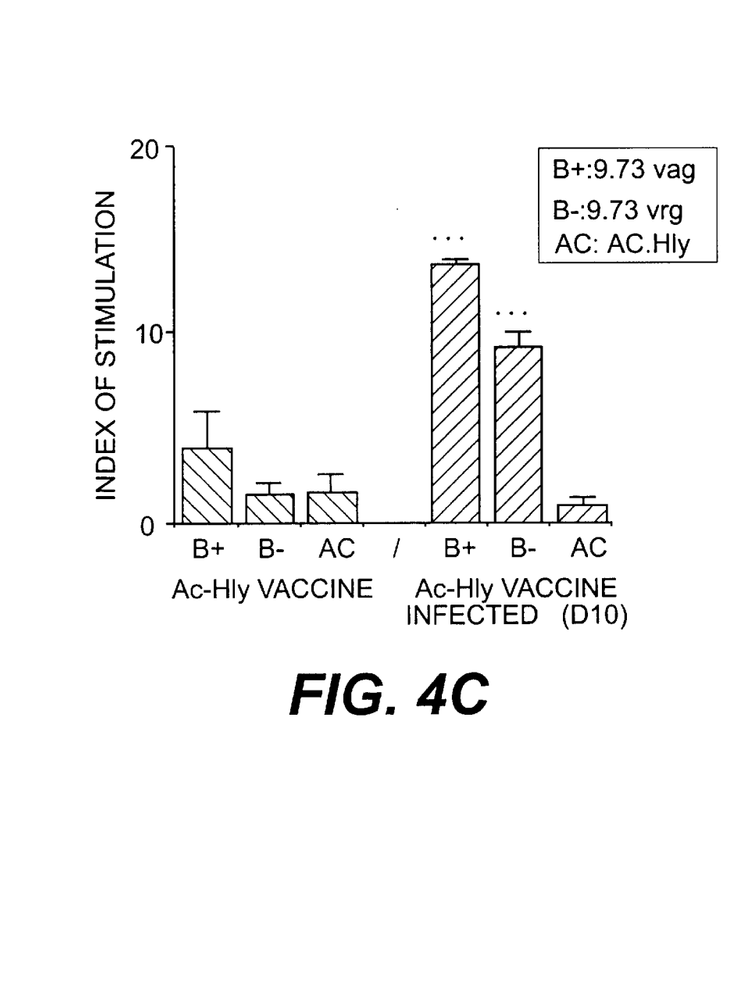
Figure 4D:
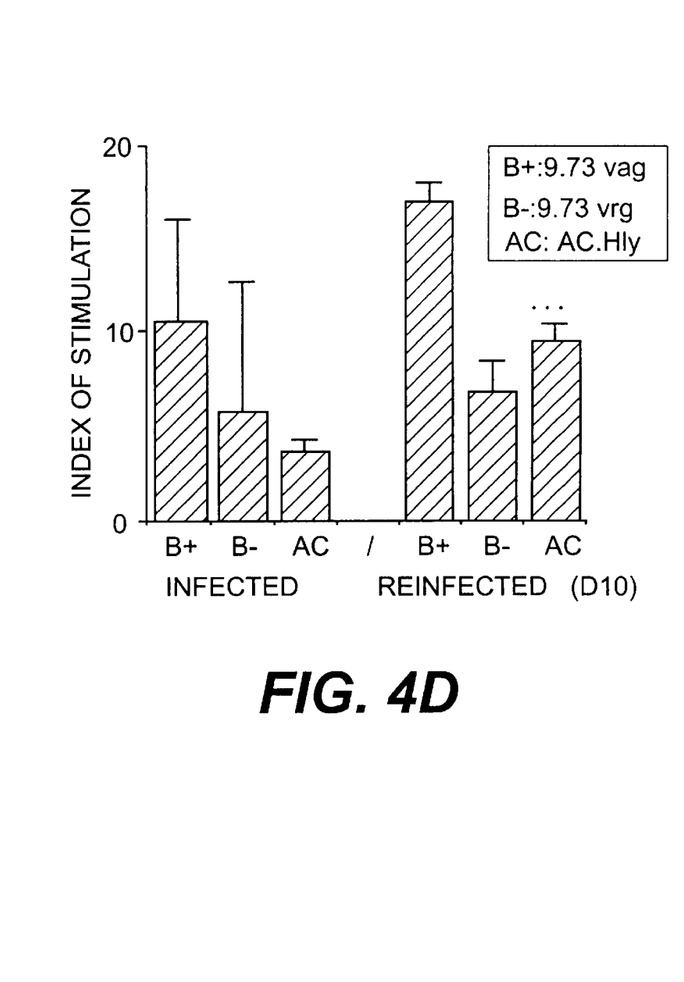
Figure 5:
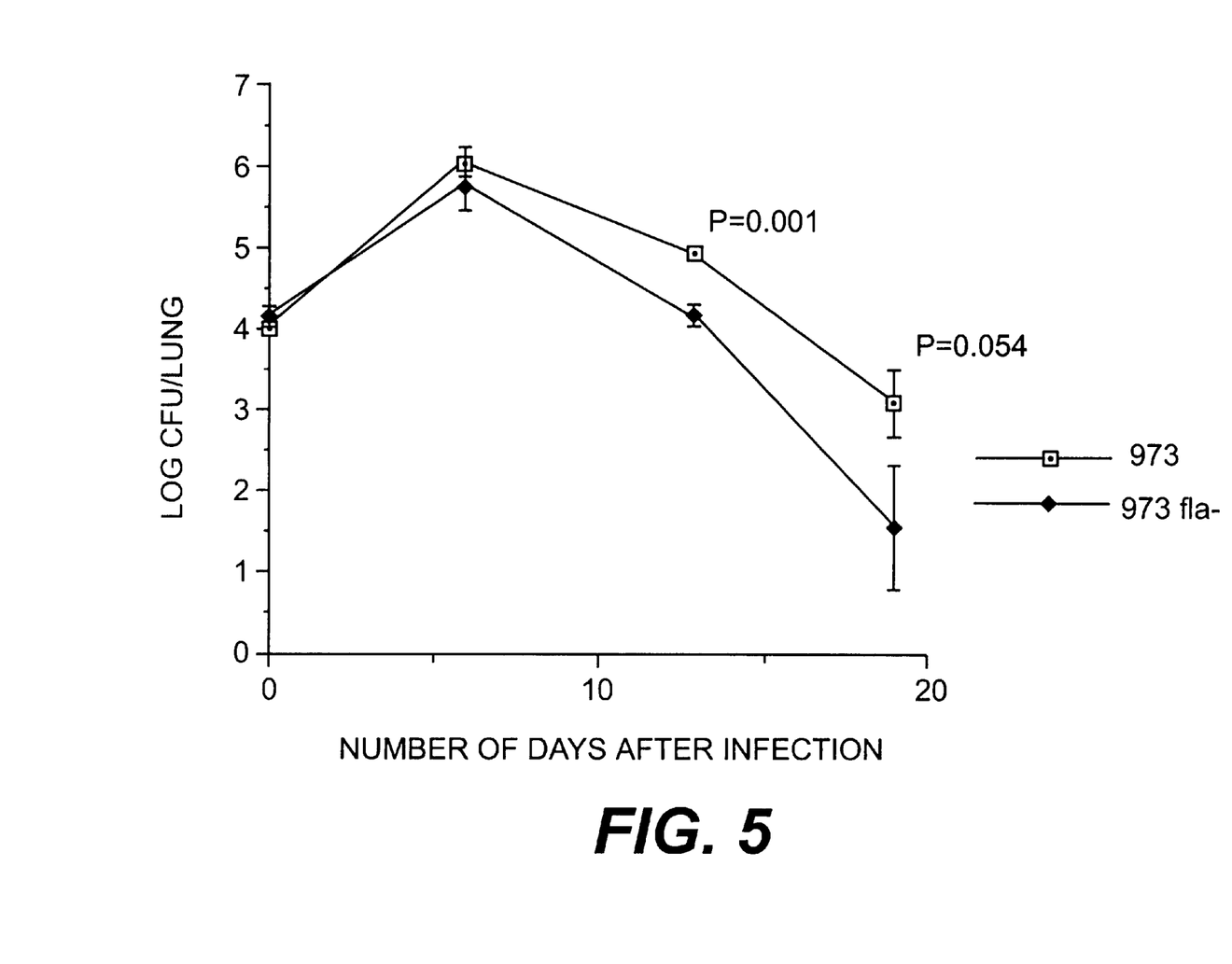
FIG. 5: Comparative virulence of *B. bronchiseptica* 973S and of an aflagellate *B. bronchiseptica* mutant (973S fla-).

Step 3. In order to persist and to evade the host's immune defences, which would have developed against the adhesins, the bacterium appears to stop the synthesis of the adhesins and then to express the proteins encoded by the vrg genes. The arguments we have in favor of this model are that:

Bordetella strains expressing either all the vag genes or the vag genes coding only for the adhesins or any vag genes are isolated during the disease, the capacity to induce lethality by the different clinical isolates of *B. bronchiseptica* varies in accordance with the amount of AC-Hly expressed and secreted after infection of guinea pigs with a culture of *B. bronchiseptica* expressing the vag genes, antibodies directed against the flagella, products of vrg genes, suggesting that the bacterium varies the synthesis of its different factors during infection, may be detected.

a *B. bronchiseptica* mutant expressing all the vag genes but not expressing flagellin (vrg product, B. J. Akerley, D. M. Monack, A. Falkow, J. H. Miller. J. Bacteriol. 1992, 174, 980–990) and which is hence immobile, constructed in the laboratory by insertional mutagenesis, is, according to our preliminary results, less virulent in the mouse model of respiratory infection: the $LD_{50}$ (median lethal dose) of the parent strain, *B. bronchiseptica* 973 S, is approximately $10^7$ bacteria and that of the fla- mutant is approximately $5\times10^7$ bacteria. Moreover, this mutant appears to be eliminated from the respiratory apparatus faster than the parent strain, suggesting the importance of the flagellum for the persistance of *B. bronchiseptica* in the host (FIG. 5). Acellular vaccine which is effective against the disease and infection induced by *Bordetella bronchiseptica*.

In agreement with the above mode, the acellular vaccine according to the invention was hence defined in order to protect not only against the toxic effect due to the different factors, but also against persistance of the bacterium. This vaccine, to be effective, consists of the factors necessary to the bacterium in order to adhere, to multiply but also to persist extra- or intracellularly, consequently to consist both of the products of the vag genes but also of the vrg genes.

To limit the cost resulting from the preparation of a vaccine consisting of all these purified factors, a cheaper acellular vaccine is the one consisting of a mixture of "urea extracts" obtained from bacteria expressing the vag genes and from bacteria expressing the vrg genes.

A "urea extract" is composed of a mixture of proteins expressed at the surface of the bacterium and which are separated from the bacterium after incubation of the latter with 5M urea. The "vag urea extract" of *B. bronchiseptica* contains, among other proteins, AC-Hly, FHA, PRN and LPS (endotoxin), and the "vrg urea extract" contains several proteins not yet characterized, the flagella and LPS.

In the case of animal bordetelloses, the sole agent of the disease is *B. bronchiseptica,* and the vaccine consists of a mixture of "vag urea extract" and "vrg urea extract" which are prepared from one or several *B. bronchiseptica* isolates if the diversity between the *B. bronchiseptica* strains, which is detected by the use of the pulse-field electrophoresis technique, lies in the proteins constituting these urea extracts. It will be important to these the need to inactivate the proteins constituting these extracts, especially AC-Hly. Moreover, it will be necessary to test the need to retain the LPS in these extracts.

Acellular vaccine which is effective against the disease and infection induced by *Bordetella pertussis* and *Bordetella parapertussis*.

In the case of human bordetelloses, *B. pertussis, B. parapertussis* and *B. bronchiseptica* may be the agents of the disease. The vaccine could then consist of bacterial suspensions expressing the vag genes and bacterial suspensions expressing the vrg genes of the representatives of the three species of Bordetella (this vaccine would then consist of six bacterial suspensions).

These bacterial suspensions could be obtained from bacteria whose toxins have been inactivated by genetic engineering so as to decrease the side effects due to vaccination with whole bacteria.

1. Preparation of vag and vrg urea extract 1.1. vrg urea extract

The vag urea extracts are prepared from phase I bacteria of the genus Bordetella (species *pertussis, parapertussis* or *bronchiseptica*), that is to say bacteria expressing the vag genes. The proteins expressed from the vag genes are, inter alia: adenyl cyclase-hemolysin (AC-Hly), pertussis toxin (PTX) and the agglutinogens (AGGs).

The protocol for preparation of these urea extracts is the same for all 3 bacterial species.

1.2. vrg urea extract

The vrg urea extracts are prepared from the same 3 phase IV bacterial species, that is to say from bacteria no longer expressing any vag gene but expressing the vrg genes. The products of these genes are not yet well characterized, with the exception of the flagella of *B. bronchiseptica*. The vrg urea extracts are prepared like the vag urea extracts.

2. Results 2.1. Preparation of vag urea extract from phase I *B. bronchiseptica* 973

2.1.1. Culture of the phase I *Bordetella bronchiseptica*

Culture the phase I bacteria on solid blood Bordet-Gengou medium (BBG; described later) for 48 hours so as to obtain isolated hemolytic colonies.

Then resuspend a few colonies in liquid Stainer medium (described later) and plate out 100 µl of this suspension on solid Stainer medium (CSM; described later).

After 24–36 hours of culture at 36° C., resuspend the bacteria in liquid Stainer medium and inoculate a 2-1 flask containing 200 ml of liquid Stainer medium such that the optical density at 650 nm is 0.05.

After inoculation, culture for 18–20 hours at 36° C. with gentle agitation so as to obtain an optical density at 650 nm of 1–1.2.

Assay the adenyl cyclase activity of the bacterial suspension thereby obtained without diluting it (described later). If this activity is between 30 and 100 U/ml, the urea extract may be prepared.

For the preparation of the vrg urea extracts, phase IV Bordetella strains are used and cultured in the same way as the phase I strains, except for the fact that the Stainer medium referred to above is supplemented with 50 mM magnesium sulfate. Where appropriate, the magnesium sulfate is replaced by other regulators, such as are described in the publication by Melton A., Weiss A., Inf. Imm. 1993, 61:807–815.

2.1.2. Preparation of the vag urea extract

Centrifuge the bacterial suspension for 30 minutes at 5000 g at 4° C.

Resuspend the bacterial pellet in 5M urea prepared in PBS buffer (described later) in the proportion of a volume equal to 5 times the wet weight of the bacterial pellet.

Leave stirring for 1 hour at 4° C., then centrifuge for 40 minutes at 40000 g at 4° C., store the supernatant at −80° C. until use, after verifying the presence of adenyl cyclase-hemolysin, filamentous hemagglutin and pertactin in the extract using antibodies specific for these factors.

2.1.3. Inactivation of the vag urea extract

After removal of the urea by passage through a G-25 column, the vag urea extract is diluted in PBS so as to obtain a protein concentration of 300 $\mu$g/ml.

Add dropwise a volume of 2.5% glutaraldehyde so as to obtain a final concentration of 0.05%.

Leave for 2 hours at room temperature, mixing regularly.

Stop the reaction by adding lysine (final concentration 0.02M).

After 2 hours at room temperature, the urea extract is adsorbed onto aluminum hydroxide prepared in PBS (1 mg/ml), overnight at 4° C. with gentle agitation. The vaccine is then ready for immunization of the animal on the basis of 10 to 20 $\mu$g/injection (described later).

2.2. Protective efficacy of the *B. bronchiseptica* vag urea extract in the mouse model of respiratory infection.

2.2.1. Immunization

Immunize two groups of mice at an interval of 14 days with either 250 $\mu$l of aluminum hydroxide at a concentration of 1 mg/ml, or 250 $\mu$l of vag urea extract adsorbed onto aluminum hydroxide.

2.2.2. Humoral response 7 days after the 2nd immunization, verify the presence of antibodies in the serum of the mice with respect to the proteins in the vag urea extract by the Western blotting technique (FIG. 1). The antibodies produced are of the IgG type, including specific immunoglobulins of the IgG2a type, and of the IgM, IgA type.

2.2.3. Cellular response

The response induced after immunization with the whole bacterium was compared with that obtained after immunization with the vag urea extract, inactivated or otherwise, or with a purified vag product, AC-Hly.

The cellular response is studied 7 days after the second immunization in a portion of the mice.

In FIG. 2, the spleen cells of mice immunized with the non-inactivated vag urea extract ($2\times10^6$ cells per ml) are cultured with either the vag urea extract (vag UE) or the vrg urea extract (vrg UE) or AC-Hly at a final protein concentration of 1 $\mu$g/ml (according to the protocol of Redhead et al.).

A proliferative response is obtained with the vag urea extract and the vrg urea extract. Cytokines characteristic of Th1 or Th2 cells are synthesized.

2.2.4 Challenge

The remainder of the mice are infected with a sublethal dose of bacteria.

14 days after the 2nd immunization, both groups of mice are infected intranasally with 50 $\mu$l of a bacterial suspension of Phase I *Bordetella bronchiseptica* cultured in Stainer medium as described above.

On $D_0$, $D_3$, $D_6$, $D_{10}$, $D_{12}$, $D_{15}$, $D_{30}$ and $D_{40}$, 3 or 4 mice from each group are sacrificed and a count of the bacteria is performed in the lung.

The results obtained are similar to those obtained after vaccination with a vaccine composed of whole bacteria (FIG. 3).

FIG. 1: Detection of specific serum antibodies after immunization with a *Bordetella bronchiseptica* vag urea extract, inactivated or otherwise 8–25% polyacrylamide gel antigen: *Bordetella bronchiseptica* urea extract after passage through a Sephadex G-25 column serum A: immune serum of mice immunized with 2×25 $\mu$g of non-inactivated *Bordetella bronchiseptica* vag urea extract serum B: immune serum of mice immunized with 2×25 $\mu$g of glutaraldehyde-inactivated *Bordetella bronchiseptica* vag urea extract.

Description of the culture media

Dehydrated Bordet-Gengou medium

Composition:

| | 1 liter | 5 liters |
|---|---|---|
| Bordet-Gengou medium | 30 g | 150 g |
| Glycerol | 10 ml | 50 ml |
| Depyrogenatedyzed water | 1 liter | 5 liters |

Adjust the pH to 7.4

Heat

Autoclave for 15 minutes at 120°

Store at 4° C.

At the time of use:

The Bordet-Gengou is enriched with 15 to 20% of sheep or horse blood. Melt the tubes and keep them melted at 54° C. Add 2.5 ml of sheep blood to each tube under sterile conditions. Pour the contents of the tube into a sterile Petri dish.

Note:

To best for *Bordetella pertussis* on a nasopharyngeal specimen, use fresh dishes (not more than 7 days at 4° C.)

CSM agar medium

To prepare 2 liters of a 10-fold concentrated solution:

| | | |
|---|---|---|
| Sodium hydrogen glutamate | (Ref. Prolabo No.27872.298) . . . | 107 g |
| L-Proline | (Ref. Merck No.7434) . . . | 2.4 g |
| NaCl | (Ref. Prolabo No.27810.295) . . . | 25 g |
| $H_2PO_4$ | (Ref. Prolabo No.26926.298) . . . | 5 g |
| KCl | (Ref. Prolabo No.26759.291) . . . | 2 g |
| $MgCl_2$ | (Ref. Prolabo No.25108.295) . . . | 1 g |
| Tris base | (Ref. Merck No.8382.2500) . . . | 15.2 g |
| Casamino acids | (Ref. Difco No.0288-01-2) . . . | 5 g |
| 1% $CaCl_2$ solution in depyrogenated water | (Ref. Prolabo No.22317.297 . . . | 20 ml |
| Depyrogenated water | QS . . . | 1 liter |

Dissolve the different constituents in a portion of the final volume of water. Adjust the pH to 7.4 using hydrochloric acid. Make to the final volume and store at −20° C.

At the time of use, mix:

100 ml of the 10-fold concentrated solution 900 ml of depyrogenated water 1 g of (2,6-di-O-methyl)cyclodextrin reference Aldrich No. 51166-71-3

15 g of Bacto agar reference Difco No. 0140-01 Distribute in 20-ml fractions in glass tubes Sterilize and add the sterile supplement.

Supplement solution:

Mix:

1 ml of 10-fold concentrated supplement solution 100 mg of glutathione reference Merck No. 4090

9 ml of depyrogenated water

Filter this solution through a 0.22 µm Millex filter Add 200 µl of this solution to 1 tube of 20 ml of medium Stainer culture medium A. Base medium To prepare 2 liters of a 10-fold concentrated solution:

| | | |
|---|---|---|
| Sodium hydrogen glutamate | (Ref. Prolabo No.27872.298) . . . | 214.0 g |
| L-Praline | (Ref. Merck No.7434) . . . | 4.8 g |
| NaCl | (Ref. Prolabo No.27810.295) . . . | 50.0 g |
| $H_2PO_4$ | (Ref. Prolabo No.26926.298) . . . | 10.0 g |
| KCl | (Ref. Prolabo No.26759.291) . . . | 4.0 g |
| $MgCl_2$ | (Ref. Prolabo No.25108.295) . . . | 2.0 g |
| Tris base | (Ref. Merck No.8382.2500) . . . | 30.5 g |
| 1% $CaCl_2$ solution in depyrogenated water | (Ref. Prolabo No.22317.297 . . . | 40 ml |
| Depyrogenated water | QS . . . | 2 liters |

Dissolve the different constituents in a portion of the final volume of water. Adjust the pH to 7.6 using hydrochloric acid. Make to the final volume and distribute this concentrated solution, which may be stored at −20° C. for several weeks.

At the time of use, dilute the medium, sterilize it at 120° C. for 15 minutes and then add the supplement sterilized by filtration.

B. Supplement solution

To prepare 200 ml of a 10-fold concentrated solution:

| | | |
|---|---|---|
| L-Cystine | (Ref. Prolabo No.23260.184) . . . | 8 g |
| Concentrated HCl | | 20 ml |

Dissolve. Into this preparation, pour the following mixture dissolved beforehand:

| | | |
|---|---|---|
| $FeSO_4.7H_2O$ | (Ref. Prolabo No.24244.232) . . . | 2 g |
| L (+) − Ascorbic acid | (Ref. Prolabo No.20155.237) . . . | 4 g |
| Nicotinic acid | (Ref. Merck No.6817) . . . | 0.8 g |
| Depyrogenated water . . . | | 120 ml |

Make to 200 ml with depyrogenated water, distribute the solution in 1-, 2-, 3- or 4-ml fractions and freeze at −20° C.

At the time of use, dilute the solution 10 times in depyrogenated water and add:

glutathione (Ref. Merck No. 4090) . . . 100 mg/10 ml of diluted supplement, sterilize this solution by filtration (Millex disposable 0.22 µm filter) and add 1 ml of sterile solution to 100 ml of sterile base medium.

Cyclase activity assay

Preparation of solutions:

Mix*

| | | |
|---|---|---|
| 1 M Tris pH8: | 4.15 ml | (83.3 mM final) |
| 0.1 M $MgCl_2$: | 5 ml | (10 mM final) |
| 0.34 M cAMP: | 29 µl | (0.2 mM final) |
| water: | 40.5 ml | |

+200 µl of [$^3$H]cAMP* so as to have $2 \times 10^4$ cpm/60 µl After homogenizing the solution, distribute in tubes in 4-ml portions and store at −20° C.

1) BSA-calmodulin mixture:

| | |
|---|---|
| BSA 10 mg/ml | 1 × µl |
| Calmodulin 2 µl | 1 × µl |
| water | 2 × µl |

BSA is diluted in the water and the calmodulin is diluted in Tris.

ATP*:
20 mM cold ATP
+[$^{32}$P]ATP*
so as to have approximately $8\times10^5$ cpm/10 µl (day 0) it is possible to use it up to $5\times10^5$ cpm/10 µl 2) Carrying out the assay:

Important: perform all the assays in duplicate, including the controls.

In each of the glass tubes labeled beforehand, mix:
60 µl of Mix*
20 µl of BSA-CaM-water
10 µl of sample (example: bacterial suspension OD=1, or dilute with 50 mM Tris pH 8)

Place the tubes in a bath at 30° C., then add 10 µl of ATP* and leave for exactly 10 minutes.

Add 200 µl of 0.5 M HCl to stop the reaction.

Immerse the tubes in a boiling water bath for 5 minutes and then add 200 µl of 1.5M imidazole. (Step unnecessary).

Allow to cool, then apply to an alumina column (1 gram per column). Elute with 3 ml of 10 mM imidazole.

Collect the eluate in 10 ml of scintillator and count the number of $^3$H cpm to calculate the column yield and the number of $^{32}$P cpm to calculate the cyclase activity. (Bear in mind quenching).

Prepare a "blank"; 10 µl of sample are replaced by 10 µl of water.

Two "total activities":
1) $^3$H: 3 ml of imidazole are eluted from a column and collected in vials containing 10 ml of scintillator and 60 µl of Mix.
2) $^{32}$P: ditto, but the vials contain 10 ml of scintillator and 10 µl of [$^{32}$P]ATP.

3) Calculations
1) Calculation of the yield of each column:

$$\frac{^{32}P \text{ cpm} \times \text{total } ^3H \text{ cpm}}{^3H \text{ cpm of the sample}} = X \text{ cpm} \ldots X', X'', X''' \ldots$$

2) Calculation of the blank:
identical=Y cpm
3) Z=total number of cpm for each sample
X cpm−Ycpm=Z cpm . . . Z', Z", Z'". . .
4) total $^{32}$P cpm→200 nmol of ATP Z cpm→W nmol
W nmol for v µl enzyme
T=time in minutes $$N \text{ nmol/minute/ml} = \frac{W \times \text{dilution factor (100 if 10 µl)}}{10 \text{ (time)}}$$

If the sample has been diluted before the assay, multiply by the dilution factor.

$$G \text{ nmol/minute/mg} = \frac{N}{\text{mg}}$$

Preparation of ATP and cAMP:
Cold ATP: once brought into suspension, use immediately or freeze at −20° C. Do not thaw and freeze several times . . . very labile! Do not store for long periods. Prepare 5 ml of 20 mM ATP: weigh approximately 70 mg and add 5 ml of 50 mM Tris pH7. On this ATP diluted to 1/1000, measure the OD very accurately to 260 nm. Calculate the exact concentration given that:

1 mM→$OD_{260}$=15.4
or $10^{-5}$ M→$OD_{260}$=0.154

Cold cAMP: prepare like ATP, it is necessary to dissolve only 32.9 mg/10 ml (it is possible to heat a little to dissolve). Likewise determine the exact concentration by measuring the OD at 260 nm, the solution being diluted to 1/500.

$10^{-5}$ M→$OD_{260}$=0.154

References of the products used
Tris: ref. 8382 from Merck
BSA, bovine albumin: ref. A-4503 from Sigma
Calmodulin or phosphodiesterase 3':5'-cyclic nucleotide activator: ref. P 2277 from Sigma
Imidazole: ref. I-0152 from Sigma
Scintillator: Optiphase <<HiSafe 3>> from LKB-Pharmacia
Cold ATP: ref A-2383 (MW=551.1) from Sigma
[$^{32}$P]ATP: Amersham, 500 µCi, ref. PB 200=alpha-$^{32}$P
Cold cAMP: A-9501 from Sigma
[$^3$H]AMP: Amersham [the smallest dose (10 µCi)]

PREPARATION OF AN ACEULLULAR VACCINE

Bordetella bronchiseptica
Adsorption onto aluminum hydroxide

Reference aluminum hydroxide Al(OH)$_3$: Alhydrogel 3% Al(OH)$_3$ equivalent to 2% Al$_2$O$_3$ (Superfos Biosector als Denmark)

Dilution buffer: phosphate buffer-0.15M NaCl pH=6.8
Formula (10-fold concentrate): 0.1M PO$_4$ (or 0.07M Na$_2$HPO$_4$.2H$_2$O
and 0.03M NaH$_2$PO$_4$.H$_2$O)
1.5M NaCl
pH=6.8
dilute 10 times in depyrogenated water at the time of use.

Washing of the aluminum hydroxide:
5 ml of concentrated Al(OH)$_3$ are washed in 50 ml of buffer, 1 to 2 times.

After the second wash, the 5 ml of washed Al(OH)$_3$ are taken up in a total volume of 50 ml, equivalent to Al(OH)$_3$ concentrated 2-fold, in fine (final concentration: 2 mg/ml).

The adjuvant thus prepared is mixed in equal volumes with the vaccine fraction and adsorption is allowed to take place overnight at 4° C. with stirring. The final concentration of Al(OH)$_3$ is 1 mg/ml in the vaccine ready for injection into the animal.

We claim:

1. A purified Bordetella strain, characterized in that it is either the *B. pertussis* strain HAV deposited at the CNCM under No. I-1485, or the *B. parapertussis* strain No. 1 deposited at the CNCM under No. I-1498.

2. The purified Bordetella strain of claim 1, which is *B. pertussis* strain HAV, deposited at the CNCM under No. I-1485.

3. The purified Bordetella strain of claim 1, which is *B. parapertussis* strain No. 1, deposited at the CNCM under No. I-1498.

* * * * *